United States Patent
Roland et al.

(10) Patent No.: US 7,792,566 B2
(45) Date of Patent: Sep. 7, 2010

(54) DEVICE FOR IMPLEMENTATION AND MONITORING OF THERMAL ABLATION AND ASSOCIATED METHOD

(75) Inventors: Joerg Roland, Gremadorf (DE); Florian Steinmeyer, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 364 days.

(21) Appl. No.: 11/837,823

(22) Filed: Aug. 13, 2007

(65) Prior Publication Data

US 2008/0058634 A1 Mar. 6, 2008

(30) Foreign Application Priority Data

Aug. 29, 2006 (DE) ........................ 10 2006 040 420

(51) Int. Cl.
*A61B 5/05* (2006.01)
*A61B 18/04* (2006.01)

(52) U.S. Cl. ........................ 600/411; 600/427; 600/421; 600/407; 606/27

(58) Field of Classification Search ................. 600/421, 600/411, 427, 407; 606/27
See application file for complete search history.

(56) References Cited

U.S. PATENT DOCUMENTS

| 5,072,162 A | 12/1991 | Sato et al. |
| 5,443,068 A | 8/1995 | Cline et al. |

FOREIGN PATENT DOCUMENTS

| DE | 199 62 666 A1 | 7/2001 |
| DE | 10 2005 003 671 A1 | 7/2006 |

OTHER PUBLICATIONS

Melodelima, D. et al. Intraluminal ultrasound applicator compatible with magnetic resonance imaging: "real-time" temperature mapping for the treatment of oespohageal tumors: an ex vivo study.*
"MRI-Guided Laser Thermal Ablation: Model and Parameter Estimates Relating MR Thermometry Images to Cell Death," Breen et al., IEEE Int. Symposium on Biomedical Imaging, Apr. 2004, pp. 296-299.
"Acoustic Surgery," Gail ter Haar, Physics Today, vol. 54, Issue 12 (2001) pp. 29-34.
"Dichte-gewichtete Phasemkodierung zur effizienten k-Raumabtastung in der NMR-Bildgebung," Greiser, Dissertation at Bayerischen Julius-Maxmillians-Universität, Würzburg, Germany (2003).

* cited by examiner

*Primary Examiner*—Eric F Winakur
*Assistant Examiner*—Helene Bor
(74) *Attorney, Agent, or Firm*—Schiff Hardin LLP

(57) ABSTRACT

A device for implementation and monitoring of thermal ablation has a device for generation of high intensity ultrasound and a magnetic resonance system for generation of examination images composed of voxels that contain temperature information. The geometry of the voxels is adapted to the shape of the ultrasound focus.

15 Claims, 1 Drawing Sheet

DEVICE FOR IMPLEMENTATION AND MONITORING OF THERMAL ABLATION AND ASSOCIATED METHOD

BACKGROUND OF THE INVENTION

1. Field of the Invention

The invention concerns a device for implementation and monitoring of thermal ablation of the type having a device for generation of high intensity focused ultrasound and a magnetic resonance system for generation of examination images composed of voxels, which examination images containing temperature information.

2. Description of the Prior Art

Non-invasive temperature determination by means of magnetic resonance thermometry has been used for some time for the monitoring thermal ablation. Examples are radio-frequency ablation, microwave ablation, laser ablation and focused ultrasound. Monitoring of the therapy result in real time during ablations procedures (particularly tumor ablations) is effected by means of MR thermometry, with the therapy being effected with non-invasive high intensity focused ultrasound (HIFU). This ablation method poses special requirements for thermometry. A high temporal resolution is required. To allow prognosis the result of the effected ablation can be implemented, a representation of the treatment region (containing the tumor) with temperature information is provided to the user; the maximum temperature or the temperature curve that is achieved can be shown. The presently used techniques for the application of non-invasive high intensity focused ultrasound enable heating of the area to be treated to more than 80° C. within 5 to 10 seconds. This is dependent on the fact that the examination images generated by means of MR that contain temperature information should be acquired in real time and be updated at intervals of 1 to 2 seconds. A high spatial resolution is additionally necessary. The expansion of the heated region is very slight and corresponds to the size of the HIFU focus. Since the temperature gradients are very steep, significant errors (caused by partial volume effects) occur with regard to the detected temperature when voxels that are too large are used in the MR examination images. The desire for a fast acquisition of the examination images with temperature information thus competes with the desire for high spatial resolution, which makes it difficult to acquire data with sufficient quality and a good signal-to-noise ratio in order exactly measure the existing temperatures.

A device for implementation and monitoring of ultrasound ablations is known from U.S. Pat. No. 5,443,068. Examination images that include temperature information are acquired with a magnetic resonance apparatus. Pathological changes such as tumors can be non-invasively treated with an ultrasound source.

Thermal ablation is also described in "Acoustic Surgery", Ter Haar, Gail, Physics Today, Vol. 54, Issue 12, pp. 29-34 (2001).

SUMMARY OF THE INVENTION

An object of the invention is to provide a device for implementation and monitoring of ablations that delivers a fast measurement and a high spatial resolution of the temperature curve.

This object is achieved in accordance with the invention by a device of the aforementioned type wherein the geometry of the voxels is adapted to the shape of the ultrasound focus.

The invention is based on the recognition that, instead of the conventional cubic (i.e. equal-sided) voxels, voxels are used having a shape that is better adapted to the geometry of the ultrasound focus.

According to a preferred embodiment of the invention, for an ultrasound focus exhibiting an ellipsoid shape the voxels can be fashioned as non-cubic parallelpiped, with the longest side of a voxel being aligned substantially parallel to the primary axis of the ultrasound focus. In this manner an ellipsoid ultrasound focus can be imaged with one or more cuboid voxels. The temperature of the examined area can be determined sufficiently precisely, and this is achieved with a reduced measurement duration.

Particularly good results can be achieved when the ratio of the longest side of a voxel relative to the longest primary axis of the ellipsoid ultrasound focus is approximately 1:3 or less in the inventive device. For instance, only three voxels with which a discrete temperature is respectively associated are necessary along the longest primary axis of the ultrasound focus.

In accordance with the invention the ultrasound focus can be imaged with 6 to 9 voxels per slice in an examination image. This is achieved by the inventive adaptation of the voxels to the shape of the ultrasound focus.

With regard to the (for the most part ellipsoid) shape of the ultrasound focus, it has proven to be advantageous when the ratio of the edge lengths of a voxel in the imaging plane is approximately 2:1 to 5:1, advantageously 3:1. A particularly good adaptation to the shape of the ultrasound focus is achieved with such a geometry of the voxels. It is also taken into account that the geometry of the ultrasound focus is not constant but rather depends on, among other things, the frequency and aperture of the transducer.

The ratio of the edge lengths of a voxel in the imaging plane can likewise correspond to the ratio of the large primary axis to the small primary axis of an ellipsoid ultrasound focus.

In addition, the invention concerns a method for generation of examination images with a magnetic resonance system, wherein the examination images composed of voxels contain temperature information and serve for monitoring of an ablation with high intensity ultrasound.

In the inventive method, the geometry of the voxels is adapted to the shape of the ultrasound focus.

DESCRIPTION OF THE PREFERRED EMBODIMENTS

Figure 1:
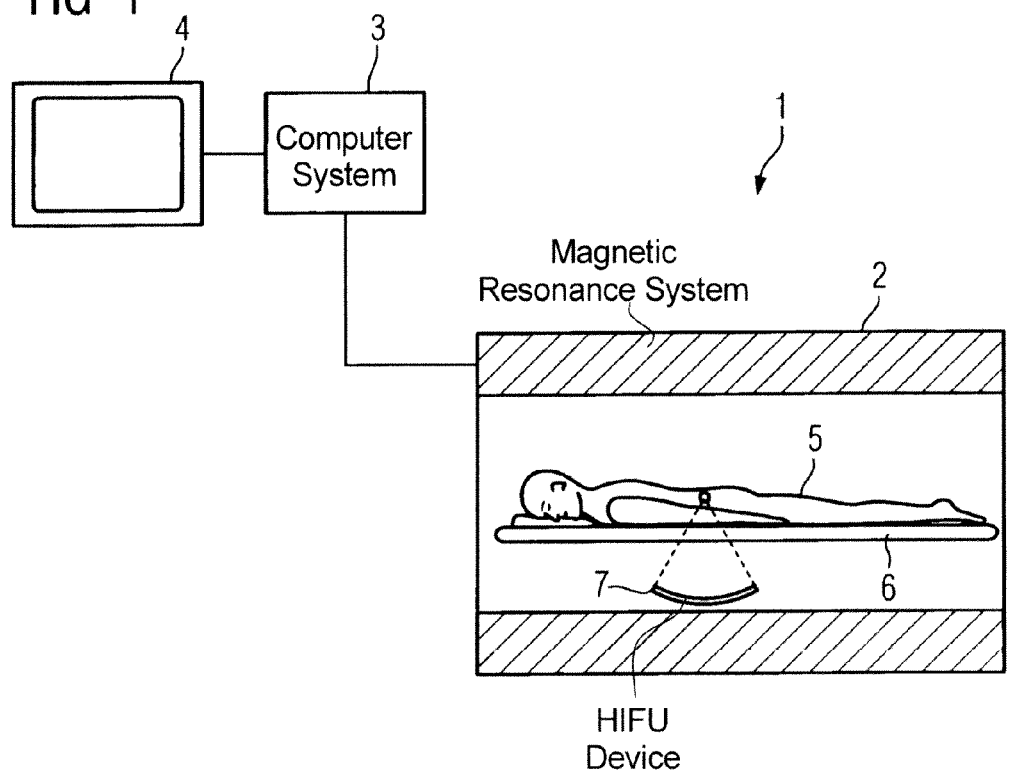
FIG. 1 schematically illustrates an inventive device.

The device 1 shown in FIG. 1 for implementation and monitoring of ablations has schematically shown magnetic resonance system 2 that is of conventional design. The magnetic resonance system 2 has a magnet for generation of a static magnetic field, a radio-frequency system as well as a schematically shown computer system 3 for controlling the radio-frequency and gradient pulses, for image reconstruction and for evaluation and operation of the magnetic resonance system 2. A monitor 4 on which examination images can be displayed is connected to the computer system 3.

As is shown in FIG. 1, a patient 5 is located on a patient bed 6 inside the magnet. A device 7 for generation of high intensity focused ultrasound (HIFU) is used for treatment of a tumor. Non-invasive tumor ablations can be effected with the device 7.

During the procedure, examination images are generated at short intervals with the magnetic resonance system 2 so that the curve of the temperature and the achieved maximum temperature can be monitored in real time during the procedure. The corresponding examination images are provided by the computer system 3 and displayed on the monitor.

Figure 2:
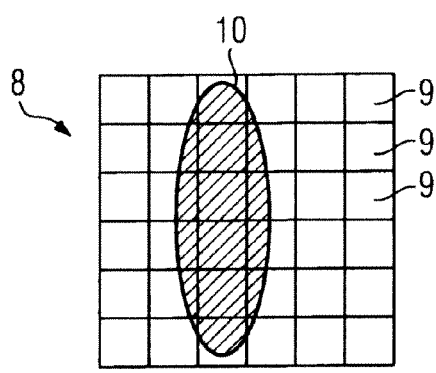
FIG. 2 shows an examination image composed of voxels according to the prior art.
Figure 3:
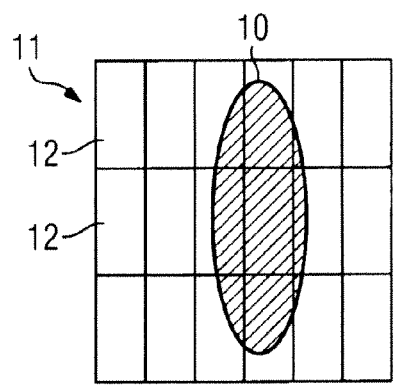
FIG. 3 shows an examination image generated with the inventive method.

The geometry of the examination images composed of voxels is shown in FIGS. 2 and 3. FIG. 2 shows an examination image composed of voxels according to the prior art and FIG. 3 shows an examination image generated with the device and the method according to the invention. Only the relevant section that contains the HIFU focus is shown by the examination images.

The conventional examination image 8 shown in FIG. 2 contains cuboid voxels 9; the geometry of the ultrasound focus 10 is additionally shown. The ultrasound focus 10 has the shape of an ellipsoid; the length of the primary axes is typically 3 mm, 3 mm and 12 mm. Only this demarcated region is heated by means of HIFU; the temperature gradients are correspondingly very steep. Given such conventional examination images the information about the temperature is frequently shown in color, for example by a color representation of the edge lines of the voxels or via colored crosses or via other known means. The temperatures of individual voxels can likewise be shown over the course of time. As can be seen in FIG. 2, approximately 18 voxels are required for the coverage of the ultrasound focus 10. Due to the large number of the required voxels 9 the generation of the examination image in conventional ways is extremely time-critical.

For comparison, in FIG. 3 an examination image 11 is shown in which non-cuboid parallelpiped voxels 12 are used instead of cubic voxels. In the shown exemplary embodiment, the ratio of the edge lengths of a voxel is approximately 2.5:1. This nearly corresponds to the ratio of the two primary axes of the ultrasound focus 10 in the imaging plane. Due to the non-cuboid parallelpiped voxels 12, in the examination image 11 shown in FIG. 3, only approximately 6-9 voxels 12 per slice are required in order to cover the entire ultrasound focus 10.

In FIG. 3 a lower number of voxels 12 do in fact indicate a relatively precise temperature, since only the middle voxels contain no spatial temperature gradients. This disadvantage is overcompensated by a significantly better signal-to-noise ratio. Improvements of the signal-to-noise ratio by a factor of 4 as well as a severely reduced measurement duration can be achieved by the changed voxel geometry.

Although modifications and changes may be suggested by those skilled in the art, it is the intention of the inventors to embody within the patent warranted hereon all changes and modifications as reasonably and properly come within the scope of their contribution to the art.

The invention claimed is:

1. A method for implementing and monitoring a thermal ablation procedure comprising:
   conducting a thermal ablation procedure by directing high intensity focused ultrasound at an ultrasound focus having an elongated focus shape encompassing tissue to be ablated in a subject;
   for an image composed of voxels representing a region of the subject encompassing said ultrasound focus, setting, in a computer, a cuboid shape of each of said voxels, as adapted voxels, dependent on said focus shape; and
   in said computer, generating said image of said region of the subject by composing said image of said adapted voxels, and including a representation of said ultrasound focus, with said cuboid shape, in said image composed of said adapted voxels.

2. A method as claimed in claim 1 comprising directing said high intensity focused ultrasound at said subject with an ellipsoid focus shape, and composing said image of non-cuboid parallelpiped adapted voxels having a longer side and a shorter side, with the longer side of each voxel being substantially parallel to the primary axis of said ellipsoid ultrasound focus.

3. A method as claimed in claim 2 comprising composing said image of adapted voxels having said longer side in a ratio to said primary axis of approximately 1:3 or less.

4. A method as claimed in claim 2 comprising generating said image as a slice image and forming said ultrasound focus in said slice image with a plurality of said adapted voxels in a range between six adapted voxels and nine adapted voxels.

5. A method as claimed in claim 2 comprising composing said image of adapted voxels having a ratio between said longer side and said shorter side is in a range between 2:1 and 5:1.

6. A method as claimed in claim 5 comprising composing said image of adapted voxels having a ratio between said longer side and said shorter side of approximately 3:1.

7. A method as claimed in claim 2 comprising composing said image of adapted voxels having a ratio between said longer side and said shorter side corresponding to a ratio between the primary axis and the secondary axis of said ellipsoid ultrasound focus.

8. A method as claimed in claim 1 comprising setting the cuboid shape of each of said adapted voxels to be the same for all of said adapted voxels.

9. A method for magnetic resonance monitoring of an ablation procedure conducted at a subject using high intensity focused ultrasound directed at the subject in an ultrasound focus having an elongated focus shape, comprising the steps of:
   acquiring magnetic resonance data from the subject during said ablation procedure, said magnetic resonance data including temperature information of tissue affected by said ablation procedure;
   for a magnetic resonance image from said magnetic resonance data composed of voxels, setting, in a computer, a cuboid shape of each of said voxels, as adapted voxels, dependent on said focus shape and
   in said computer, generating said magnetic resonance image of said region of the subject by composing said image of said adapted voxels, and including a representation of said ultrasound focus, with said cuboid shape, in said image composed of said adapted voxels.

10. A method as claimed in claim 9 comprising directing said high intensity focused ultrasound at said subject with an ellipsoid focus shape, and composing said magnetic resonance image of non-cuboid parallelpiped adapted voxels having a longer side and a shorter side, with the longer side of each voxel being substantially parallel to the primary axis of said ellipsoid ultrasound focus.

11. A method as claimed in claim 10 comprising composing said magnetic resonance image of adapted voxels having said longer side in a ratio to said primary axis of approximately 1:3 or less.

12. A method as claimed in claim 10 comprising generating said magnetic resonance image as a slice image and forming said ultrasound focus in said slice image with a plurality of said adapted voxels in a range between six adapted voxels and nine adapted voxels.

13. A method as claimed in claim 10 comprising composing said magnetic resonance image of adapted voxels having a ratio between said longer side and said shorter side adapted in a range between 2:1 and 5:1.

14. A method as claimed in claim 13 comprising composing said magnetic resonance image of adapted voxels having a ratio between said longer side and said shorter side of approximately 3:1.

15. A method as claimed in claim 9 comprising setting the cuboid shape of each of said adapted voxels to be the same for all of said adapted voxels.

\* \* \* \* \*